United States Patent [19]

Kozam et al.

[11] 4,381,778
[45] May 3, 1983

[54] NEEDLE-LOADING MULTIPLE BARREL SYRINGE

[76] Inventors: George Kozam, 234 E. Clinton Ave., Tenafly, N.J. 07670; Pat Romanelli, 224 Brook St., Harrington Park, N.J. 07640

[21] Appl. No.: 267,679

[22] Filed: May 27, 1981

[51] Int. Cl.³ .............................................. A61M 5/00
[52] U.S. Cl. ..................................... 604/191; 604/249
[58] Field of Search ................ 128/218 NV, 274, 215, 128/218 R, 218 M, 220, 221, 234; 222/129, 135, 388, 390, 402.23, 406, 407, 544

[56] References Cited

U.S. PATENT DOCUMENTS

| | | | |
|---|---|---|---|
| 2,094,888 | 10/1937 | Hooper | 128/274 X |
| 2,208,032 | 7/1940 | Hooper | 128/274 X |
| 2,709,433 | 5/1955 | Kauzal | 128/234 X |
| 4,109,653 | 8/1978 | Kozam et al. | 128/218 NV |

FOREIGN PATENT DOCUMENTS 207338  2/1968  U.S.S.R. ...................... 128/218 NV

Primary Examiner—John D. Yasko
Attorney, Agent, or Firm—Edward F. Levy

[57] ABSTRACT

A multiple barrel syringe for selective delivery of a plurality of fluids through a single needle is adapted to be loaded with each of said fluids through the needle thereof. The syringe body includes a pair of fluid-retaining bores, each containing a plunger and each communicating with the single needle through restrictive conduits in which respective flexible sealing valves are interposed. As each plunger is depressed, the respective valve is depressed and distorts under pressure of the fluid, allowing the fluid to flow to the needle. For filling each bore through the needle, a plunger is manually depressed to compress and distort the respective valve, enabling fluid to flow from a container through the needle and through the unobstructed conduit to the selected bore in response to raising of the plunger.

10 Claims, 5 Drawing Figures

FIG. 1
FIG. 2
FIG. 3
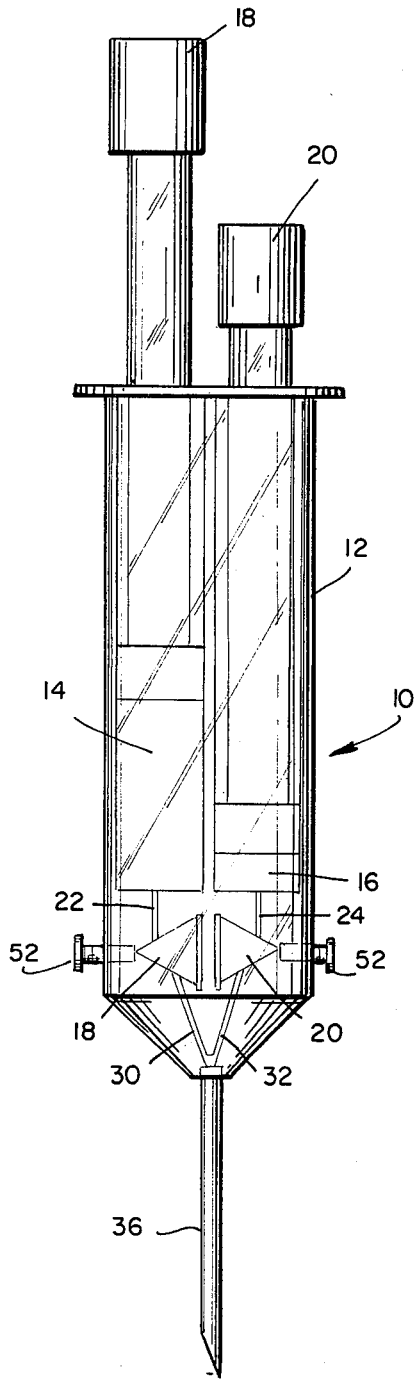
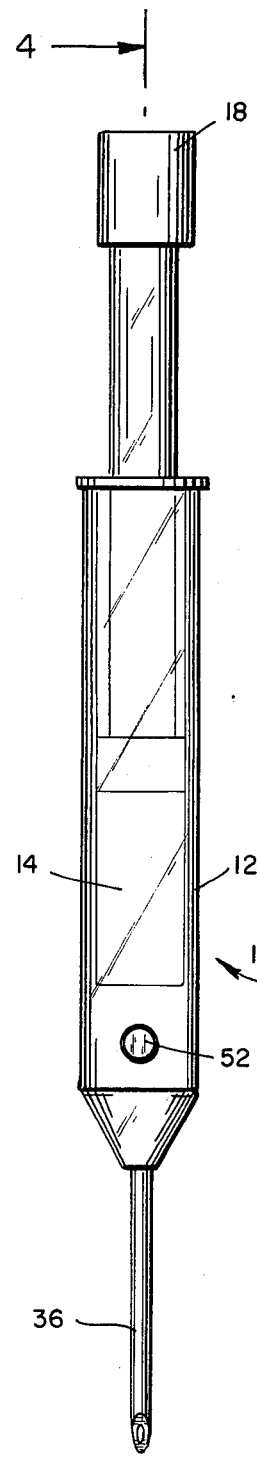
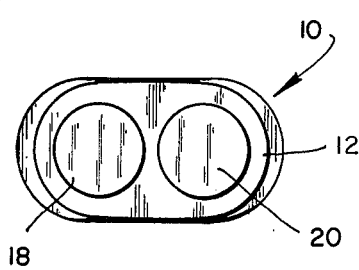

NEEDLE-LOADING MULTIPLE BARREL SYRINGE

The present invention relates to hypodermic syringes generally used in the medical and dental fields, and is particularly directed to a multiple barrel syringe for the successive dispensing of different fluids in a prearranged selected manner. The multiple barrel syringe of this invention is constructed to permit each of the barrels to be loaded with a different fluid through the common needle thereof.

In our U.S. Pat. No. 4,109,653, filed Aug. 29, 1978, and entitled "Multiple Barrel Syringe", we have disclosed a successive delivery multiple syringe which comprises a body formed with a pair of bores, each containing a different fluid to be dispensed, each of said bores containing a slidable plunger. The syringe mounts a single needle through which the fluid is dispensed, and each bore communicates with the needle through a respective one-way valve in the nature of a rubber duck-bill valve. Depression of either of the plungers produces fluid pressure in the associated bore which opens up its one-way valve to enable the fluid from said bore to pass through the needle. Mixing of the fluids within the syringe from one bore to the other is eliminated or made negligable by the inclusion of the one-way valve to the needle.

The syringe shown in U.S. Pat. No. 4,109,653 is particularly adapted for use in dental root canal therapy in which debrided particles are removed by first injecting hydrogen peroxide under pressure into the root canal, and immediately thereafter injecting a chlorinated soda solution such as sodium hypochlorite into the root canal. Since two syringes are normally required for this successive injection, the use of a single syringe having two barrels containing the different fluids was found beneficial and effective in decreasing the time between successive injections and reducing the number of syringes used with a consequent saving of time of loading and sterilization.

Because the syringe of the aforementioned patent included one-way valves to prevent fluid from one bore from mixing with the fluid in the other bore, it was not possible to fill the syringe by drawing fluid upwardly through the needles. Filling of the bores was only possible by removing the plungers therefrom and pouring the selected fluid individually into the opened tops of the bores. This is often a cumbersome and time-consuming procedure, especially in root canal therapy where it is desirable to fill the syringe barrels in a rapid manner from vessels containing the selected fluids. In addition, the removal of the plungers for barrel-loading of the syringe may result in contamination of the otherwise sterile syringes.

It is an object of the present invention to provide a multiple barrel syringe of the type described which is constructed to permit loading of each of its barrels through a single needle, without removal of the plungers.

Another object of the invention is the provision of a multiple barrel syringe of the character described which includes control valves which operate to prevent the fluids in the barrels from mixing during operation of the syringe, and which are also operable to permit the barrels to be individually filled through the common needle.

A further object of the invention is to provide a multiple barrel syringe which can be loaded through a single needle from a single source to avoid multiple capsule type loading and thus assure the same uniform type medicament or other solution from a single homogenous batch.

In accordance with the invention herein, there is provided a successive delivery multiple barrel syringe having a body formed with a pair of bores, each containing a depressible plunger, and each communicating with a single needle. Each bore terminates in a narrow conduit leading to a recess containing a flexible and compressible cone-shaped valve. Each valve recess communicates through a second narrow conduit with the hollow needle of the syringe. The cone-shaped valve normally fills the interior of the recess in which it is housed and prevents the fluid in the opposite bore from flowing into the interior of its communicating bore during operation of the syringe. A manually-operable member is associated with each cone-shaped valve for selective compression and deformation of said valve when said syringe is to be filled, thereby bringing said second conduit into communication with the first conduit through the valve recess and enabling the associated bore to be filled through the needle.

Additional objects and advantages of the invention will become apparent during the course of the following specification when taken in conjunction with the accompanying drawings, in which:

FIG. 1 is a front elevational view of a multiple barrel syringe made in accordance with the present invention;

FIG. 2 is a side elevational view thereof;

FIG. 3 is a top plan view thereof;

Figure 4:
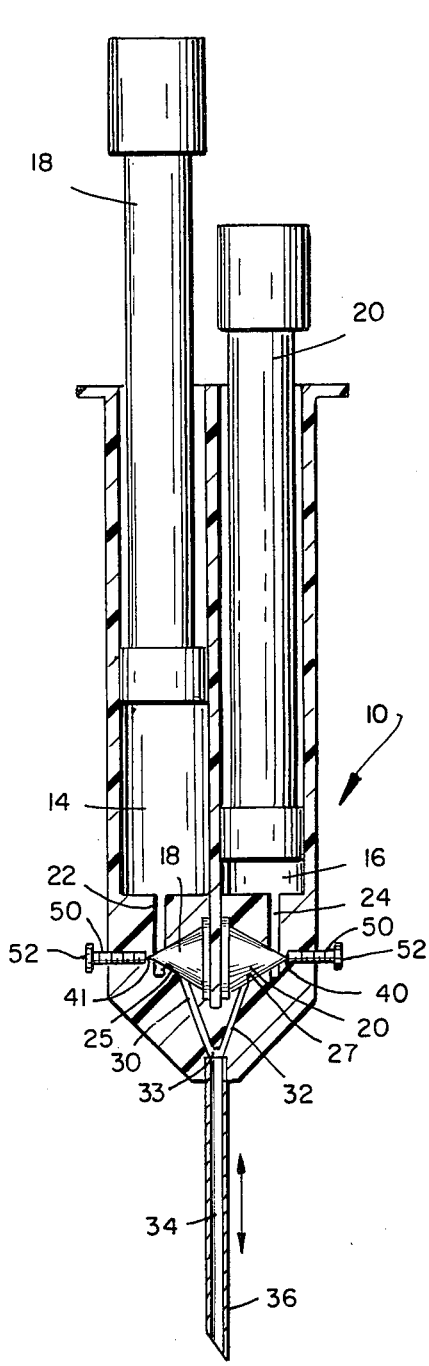
FIG. 4 is a sectional view taken along line 4—4 of FIG. 1.

Referring in detail to the drawings, there is shown a successive delivery multiple barrel syringe 10 made in accordance with the present invention and comprising a body 12 having dual spaced bores 14, 16, each of which, contains a respective slidable plunger 18, 20.

At their lower ends, the bores 14 and 16 terminate in respective conduits 22 and 24 of reduced diameter for the transmission of fluids from said bores in response to depression of the respective plungers 18 and 20 in said bores. The conduits 22 and 24 extend to and open into respective cone-shaped recesses 25 and 27 which house valves 26 and 28.

Each of the valve recesses 25 and 27 communicate, through respective second conduits 30 and 32 of small diameter, with a hollow syringe needle 36 mounted at the bottom of the syringe body. The second conduits 30 and 32 depend from the respective valve recesses 25, 27 and are inclined inwardly, meeting at a junction 33 which communicates with the central bore 34 of the hollow needle 36, as shown in FIGS. 4 and 5.

It will be seen that the valve recesses 25 and 27 are cone-shaped, having a apex end 38 located adjacent to an outer side of the syringe body and a base end 40 located adjacent the center of the syringe body and formed with a peripheral flange 42. Each of the first conduits 22, 24 communicates with the respective valve recess adjacent its base end portion 40, while each of the second conduits 30, 32 communicates with the apex end portion 38 of the respective valve recess.

Each of the valves 26, 28 is made in the form of a hollow, cone-shaped membrane or cup which is made of a flexible and deformable material such as rubber, having a shape-retaining memory. The valves 26, 28 are made of the same size and shape as the interior of the valve recesses 25, 27 so that they fit snugly within the latter and normally fill the interior of the valve recesses, as shown in full line in FIG. 5, with no appreciable air space between the inner surfaces of the recesses and the outer surfaces of the valves. Each of the valves 26, 27 has a base portion formed with a peripheral flange 44 which is seated within the peripheral flange portion 42 of the respective recess 25, 27, thereby retaining the valves in mounted position.

Figure 5:
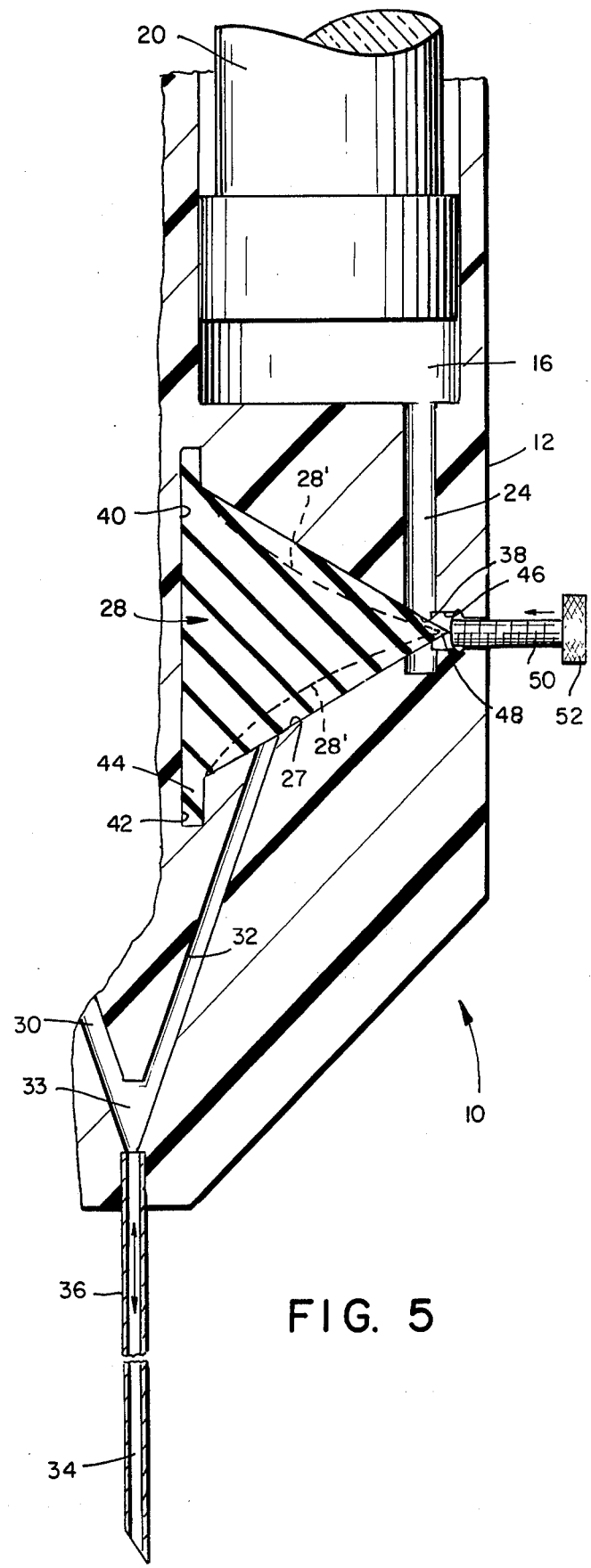
FIG. 5 is an enlarged fragmented sectional view of a portion of the syringe as shown in FIG. 4.

The apex ends 38 of each of the valve recesses 25, 27 are snubbed or cut off, as shown in FIG. 5, and communicate with a cylindrical bore 46 of larger diameter. The apex or tip 48 of each valve 26, 28 projects through the snubbed apex end 38 of the respective valve recess 25, 27, and extends into the cylindrical bore 46. Slidably mounted in each cylindrical bore 46 is a button or finger piece 50 having at its end an enlarged head 52 located exteriorly of the syringe body in a position to be engaged and manually depressed by the user to deform the adjacent valve, for purposes of filling the syringe, in a manner to be described in detail.

When the syringe 10 is ready for use in dispensing fluids, the bores 14 and 16 are filled with different fluids and the plunger 18 and 20 are in extended position. If fluid is first to be dispensed from bore 16, for example, the syringe is held in one hand in the usual manner, and the plunger 20 is depressed by the thumb, applying pressure to the fluid within the bore 16 and within its communicating first conduit 24. The pressurized fluid within conduit 24 engages the flexible cone-shaped valve 28 at its apex portion 46, and constricts and distorts the wall of the valve sufficiently to provide a passageway between the valve body and the surface of the conical recess 27, so that the fluid flows from the first conduit 24, around the body of valve 28, to the second conduit 32 and then to the base 34 of needle 36. The same action occurs when the plunger 18 is subsequently depressed to feed the fluid in bore 14 to the needle 36. In each instance, the pressure of the fluid distorts the body of the respective flexible valve within its associated recess to such an extent that the pressurized fluid forms its own path through the valve recess from the first conduit 22 or 24 to the second conduit 30 or 32.

The valves 26 and 28 serve to prevent fluid from one bore 14 or 16 from entering into the opposite bore and mixing with the fluid therein. Thus, when the plunger 18, for example, is depressed to feed fluid from bore 14 through the second conduit 30 to the needle 36, some of this fluid may be diverted upwardly, via junction 33, through the opposite second conduit 32. Since the second conduit 32 communicates with the base end portion of the valve 28, the force of this diverted fluid is not sufficient to warp or deform the valve body at its wide base portion, and the body of valve 28 blocks further travel of the diverted fluid so that it does not enter valve recess 27 and, therefore, cannot reach bore 16.

As previously indicated, the primary purpose of the multiple barrel syringe of the present invention is to permit each of the bores to be loaded with fluid through the syringe needle. It will be appreciated that since the cone-shaped valves 26, 28 completely fill the correspondingly-shaped valve recesses 25, 27, if it were attempted to fill one of the bores, for example, the bore 16, by inserting the tip of needle 36 in a container of fluid and pulling the plunge 20 upwardly, the tip or apex portion 48 of the valve 28 seals off the lower end of first conduit 24, thereby preventing the suction created within bore 16 from being applied through second conduit 32 and the hollow needle 36 to the fluid. The buttons 50 are provided to upset this seal created by the valve, and to permit needle loading.

When it is desired to fill bore 16 by drawing fluid upwardly through the needle 36, the syringe body 12 is held in one hand with the needle immersed in the fluid, and the button 50 held depressed by the thumb or finger. The other hand grasps the plunger 20 and pulls it upwardly to an extended position.

Depression of the button 50 causes it to slide inwardly through cylindrical bore 46 so that the end of the button engages and presses inwardly upon the protruding tip or apex 48 of valve 28. This pressure upon the tip 48 in a direction along the axis of valve 28, causes the flexible cone-shaped valve to deform in such a mamnner that its walls bow inwardly as indicated by the broken lines 28' in FIG. 5. This deformation of the valve 28 breaks the seal which it would normally create, and clears the ends of the first and second conduits 24 and 32 for the passage of fluid therethrough. Thus, when the plunger 20 is elevated, the suction created in bore 16 is applied through first conduit 24, valve recess 27, second conduit 32 and the bore 34 of needle 36 to the fluid. Fluid is thus drawn through the needle 36, second conduit 32, valve recess 27 and first conduit 24 to the bore 16 until the bore 16 is filled to the desired extent.

It will be appreciated that the same procedure is followed for filling the outer bore 14 through the needle 36, by depressing the opposite button 50 adjacent valve 26 and withdrawing plunger 18.

After the needle-loading of each of the bores has been completed, the button 50 is released and the flexible cone-shaped valve returns to its original shape, its tip pressing against the end of the depressed button 50 and sliding it back to its extended position.

While a preferred embodiment of the invention has been shown and described herein, it is obvious that numerous omissions, changes and additions may be made in such embodiment without departing from the spirit and scope of the invention.

What is claimed is:

1. A multiple barrel syringe for the selective dispensing of fluids, comprising:

a body portion having a plurality of fluid-retaining bores, a plurality of individually-depressible plungers extending respectively into said bores, a single hollow needle mounted on said body portion, and fluid conduit means connecting each of said bores with the interior of said hollow needle, said fluid conduit means comprising a first fluid conduit communicating with each of said bores, a valve recess communicating with each first fluid conduit, and a second fluid conduit communicating at one end with said valve recess and at the other end with the interior of said hollow needle, a flexible valve member housed in each of said valve recesses and normally filling the interior thereof with the body of the valve member covering and sealing off the communicating ends of said first and second fluid conduits against passage of fluid upwardly through said conduits, and a movable seal-release member movably mounted adjacent each respective valve recess, each seal-release member having a portion projecting outwardly from the exterior of said syringe body portion and positioned to be selectively and manually actuated to move said seal release member into engagement with the valve member in said recess in a direction to engage and deform said valve member sufficiently to unseal the communicating ends of said first and second fluid conduits, whereby to permit fluid to be drawn upwardly through said needle to the bore communicating with the valve recess containing said deformed valve member, in response to withdrawal of the plunger in said bore, whereby each of said bores may be filled independently with a different fluid through the single needle.

2. A multiple barrel syringe according to claim 1 in which each of said valve recesses is cone-shaped, and each valve member is hollow, cone-shaped, and of size to fit snugly within the interior of the valve recess in which it is housed.

3. A multiple barrel syringe according to claim 2 in which each cone-shaped valve recess has a wide base portion located centrally within the needle body and a narrow apex portion located proximate the side wall of said syringe body.

4. A multiple barrel syringe according to claim 3 in which each first fluid channel communicates with the apex portion of a respective valve recess and each second fluid channel communicates with the base portion of a respective valve recess.

5. A multiple barrel syringe according to claim 4 in which each movable seal-release member is aligned with the tip of the cone-shaped valve member housed in a respective valve housing, and is mounted for movement in a direction to press said valve member tip inwardly along the axis of said valve member.

6. A multiple barrel syringe according to claim 5 in which said valve member is sufficiently flexible to cause its walls to bow inwardly upon depression of said valve member tip by said seal-release member, whereby said walls are spaced from the communicating first and second fluid conduits.

7. A multiple barrel syringe according to claim 4 in which the apex portion of each valve recess is cut off to permit the tip of the cone-shaped valve member housed therein to project therefrom in a position to be engaged by said seal-release member.

8. A multiple barrel syringe according to claim 7 in which the cut-off apex portion of each cone-shaped valve recess communicates with a bore extending through said syringe body to the exterior thereof, and in which each seal-release member is slidably mounted in said bore and includes an elongated body having an end portion projecting from said syringe body in a position to be manually depressed by the user of said syringe.

9. A multiple barrel syringe according to claim 8 in which said seal-release member is aligned with the projecting tip of the adjacent valve member and is sized to press inwardly upon said tip when said seal-release member is depressed, thereby causing said flexible valve member to deform in such a manner that its walls are bowed inwardly.

10. A multiple barrel syringe according to claim 9 in which the inward bowing of said valve member walls provide a clear passage for flow of fluid from the second fluid conduit to the first fluid conduit through said valve recess and around the body of said deformed valve member.

* * * * *